United States Patent [19]
Hudetz et al.

[11] Patent Number: 5,981,432
[45] Date of Patent: Nov. 9, 1999

[54] SYNERGISTIC HERBICIDAL COMPOSITIONS OF S-METOLACHLOR

[75] Inventors: Manfred Hudetz, Rheinfelden, Switzerland; Dan Worden Kidder, Kernersville, N.C.; Robert Franklin Milliken, Calgary, Canada; Norbert Nelgen, Jugenheim, Germany

[73] Assignee: Novartis Crop Protection, Greensboro, N.C.

[21] Appl. No.: 08/930,901

[22] PCT Filed: Apr. 1, 1996

[86] PCT No.: PCT/EP96/01431

§ 371 Date: Feb. 2, 1998

§ 102(e) Date: Feb. 2, 1998

[87] PCT Pub. No.: WO96/32013

PCT Pub. Date: Oct. 17, 1996

[30] Foreign Application Priority Data

Apr. 12, 1995 [CH] Switzerland ............... 1072/95

[51] Int. Cl.⁶ .............. A01N 25/32; A01N 37/18; A01N 43/54; A01N 57/02
[52] U.S. Cl. ............ 504/105; 504/127; 504/133; 504/134; 504/136; 504/149
[58] Field of Search ............... 504/149, 105, 504/127, 133, 134, 136

[56] References Cited

U.S. PATENT DOCUMENTS 5,002,606  3/1991  Moser et al. .................. 71/118
5,407,898  4/1995  Quadranti et al. ............ 504/136

FOREIGN PATENT DOCUMENTS 282613   9/1988  European Pat. Off. .
318433   5/1989  European Pat. Off. .
3536035  4/1987  Germany .

OTHER PUBLICATIONS

Research Disclosure No. 37242, pp. 271–272, Apr. 1995.
Derwent Abstract 95–151785/20 (of Japanese 07 076 504) 1995.
Moser et al. Abstract 99:48882 (CA Database) of "Atropisomerism, chiral center and activity of metolachlor", Pesticide Chemistry: Human Welfare Environ., Proc. 5th Int. Congr. Pesticide Chem. vol. 1, 315–320, 1982.

*Primary Examiner*—S. Mark Clardy
*Attorney, Agent, or Firm*—William A. Teoli, Jr.; John D. Peabody, III

[57] ABSTRACT

Herbicidal compositions comprising S-metolachlor and at least one additional herbicide selected from atrazine, terbuthylazine, flumetsulan, pendimethalin, metosulam, pyridate, glyphosate, glufosinate, cyanazine, dicamba, halosulfuron, prosulfuron, primisulfuron, sulcotrione, metribuzin, BAY FOE 5043, and salts thereof. The compositions may also contain the safener benoxacor.

13 Claims, No Drawings

SYNERGISTIC HERBICIDAL COMPOSITIONS OF S-METOLACHLOR

This application has been filed under 35 USC 371 as the national stage of international application PCT/EP 96/01431, filed Apr. 1, 1996.

The present invention relates to a novel herbicidal composition which comprises a combination of herbicidally active ingredients which is suitable for selectively controlling weeds in crops of useful plants, for example in crops of cereals, maize, rice, oilseed rape, sugar beet and sugar cane, in plantation crops, and in crops of cotton and soybeans.

The invention furthermore relates to a method of controlling weeds in crops of useful plants and to the use of this novel composition therefor.

Herbicidal compositions which comprise metolachlor in combination with other known herbicides are compiled, for example, in Research Disclosure No. 37242, Apr. 1995.

Surprisingly, it has now been found that a combination of a certain optical isomer of metolachlor with at least one active ingredient from the abovementioned Research Disclosure, in a ratio varying within specific limits, has a herbicidal action which is capable of effectively controlling the majority of weeds occurring in crops of useful plants preemergence as well as postemergence without causing considerable damage to the useful plant.

The optical isomer of metolachlor which is suitable according to the invention is a RS,1'S(-)-N-(1'-methyl-2'-methoxyethyl)-N-chloroacetyl-2-ethyl-6-methylaniline, of the formula A

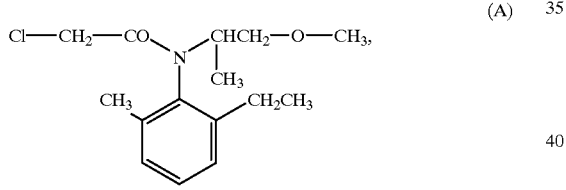
(A)

which is described, for example, in U.S. Pat. No. 5,002,606.

Accordingly, the present invention provides a novel herbicidal composition for selectively controlling weeds which comprises, as active ingredient, the compound of the formula A

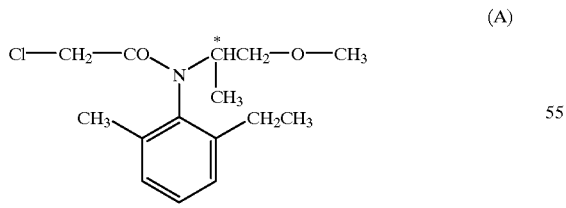
(A)

and a synergistically effective amount of at least one active ingredient from amongst the substance classes of the formula I

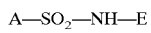
A—SO$_2$—NH—E  (I)

in which

A is a radical of the formula

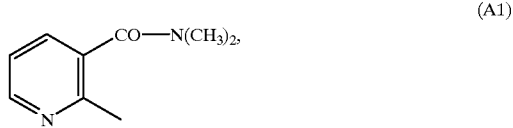
(A1)

(A2)

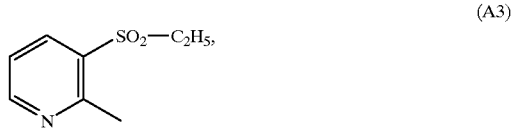
(A3)

(A4)

(A5)

(A6)

(A7)

(A8)

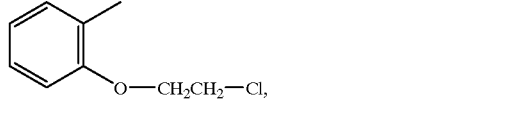
(A9)

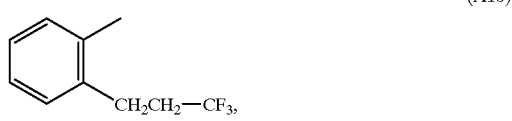
(A10)

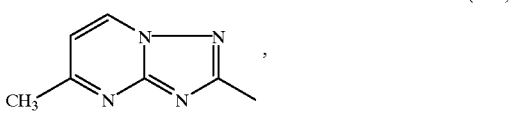
(A11)

-continued (A12) 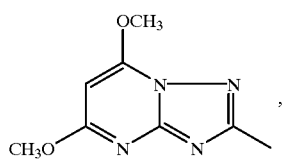

(A11) 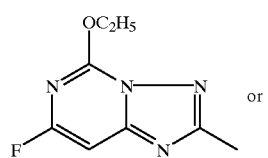 or (A14) 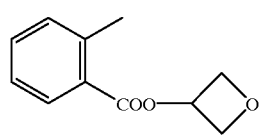

(E1) 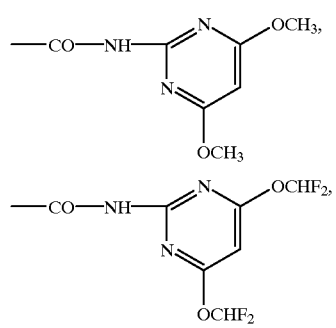

(E2)

(E3)

(E4)

(E5)

(E6) 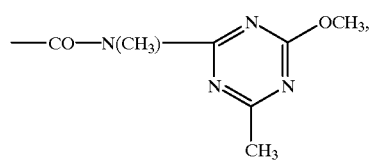

-continued (E7) 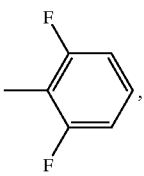

(E8) 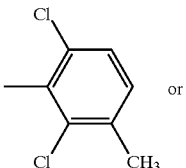 or (E9) 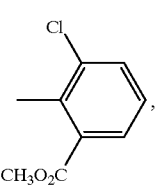

of the formula II $$\text{(II)}$$

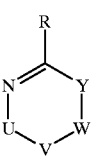

in which

U—V is a radical of the formula $CR_1$=N, N=$CR_1$ or $NR_1CO$, in which $R_1$ is —$NHC_3H_7$-i, —$NHC(CH_3)_2CN$, —$NHC_4H_9$-t, —$NHC_2H_5$, —$SCH_3$, $CH_3$, —Cl,

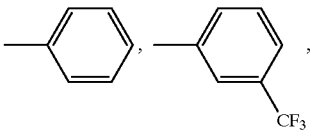

W—Y is a radical of the formula $CR_2$=N, N=$CR_2$, $NR_2CO$ or $CR_2$=$CR_3$, where $R_2$ is hydrogen, —Cl, —$NH_2$, —$NHC_3H_7$-i or —$NHC_2H_5$ and $R_3$ is —$NH_2$, —$NHCH_3$ or —O—CO—$SC_8H_{17}$ and R is —Cl, —$SCH_3$, —$C_4H_9$-t,

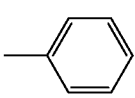

or hydrogen, of the formula III
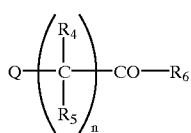
(III)
in which
n is 0 or 1,
$R_4$ is hydrogen,
$R_5$ is hydrogen, —$CH_3$ or —$NH_2$,
$R_6$ is hydroxyl, —$OC_2H_5$, —O—$CH(CH_3)_2$—$CO_2C_2H_5$, —$NHSO_2CH_3$, —$OCH_3$, —$OC_4H_9$-n or —$OCH_2$—C≡CH
and
Q is a radical of the formula
—$CH_2CH_2$—P(O)(OM)$CH_3$, (Q1)
—$NHCH_2$—P(O)(OM)$_2$ (Q2)
in which M is an alkali metal, ammonium, alkylammonium, sulfonium or alkylsulfonium,
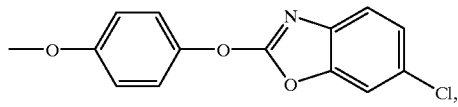 (Q3)
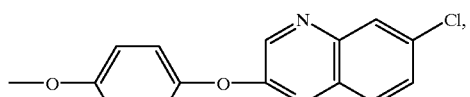 (Q4)
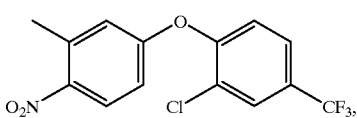 (Q5)
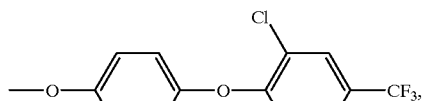 (Q6)
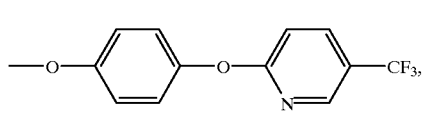 (Q7)
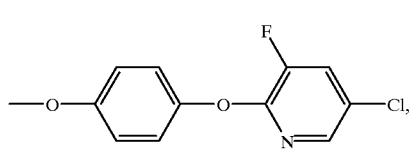 (Q8)
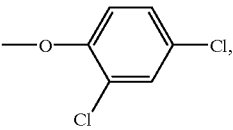 (Q9)
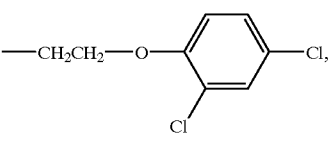 (Q10)
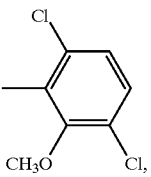 (Q11)
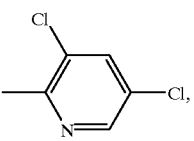 (Q12)
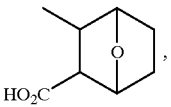 (Q13)
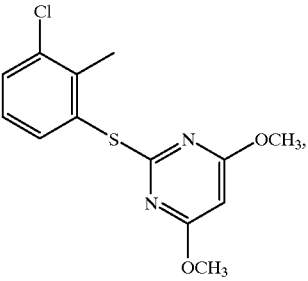 (Q14)
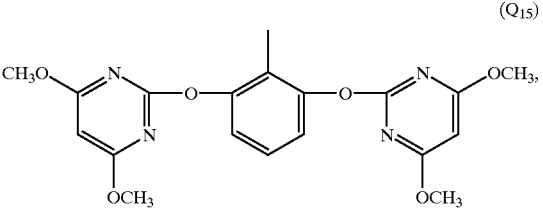 (Q15)
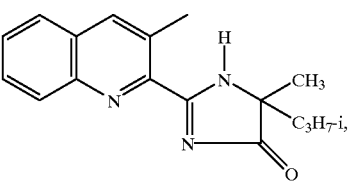 (Q16)

-continued (Q17)
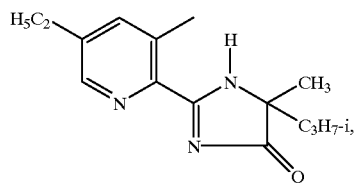

(Q18)
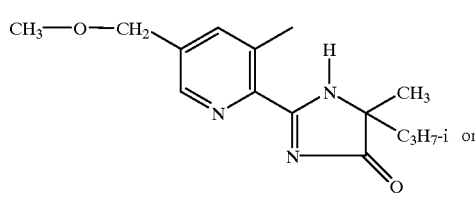

(Q19)
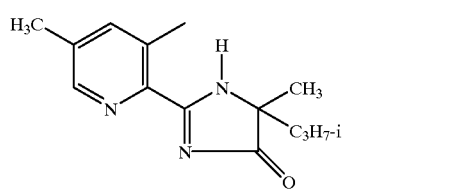

or (Q20)
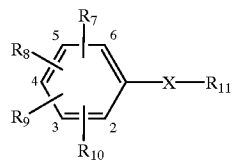

of the formula IV (IV)

in which
R$_7$ is 2—NO$_2$ or 2—Br,
R$_8$ is 6—NH$_2$ or 6—Br, or
R$_8$ and R$_7$ together form a radical of the formula —CH(CH$_3$)$_2$—CH(OC$_2$H$_5$)O— which bridges positions 2 and 3 of the phenyl radical and where the carbon atom of this radical is linked with position 2 and the oxygen atom of this radical with position 3,
R$_9$ is 3—CH$_3$, 4—CF$_3$ or 4—CN,
R$_{10}$ is hydrogen or 4—CH$_3$,
X is —O—, —NH—, —NC$_3$H$_7$-n- or —NC$_2$H$_5$- and
R$_{11}$ is hydrogen, —CH(C$_2$H$_5$)$_2$, —C$_3$H$_7$-n, —CH$_2$—C(CH$_3$)=CH$_2$, —CO—C$_8$H$_{17}$-n-, —CO—C$_7$H$_{15}$-n or —SO$_2$CH$_3$,
of the formula V (V)
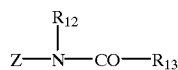

in which

Z is a radical of the formula (Z1)
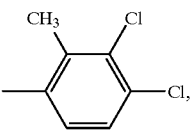

(Z2)
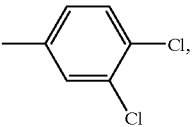

(Z3)
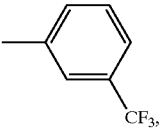

(Z4)
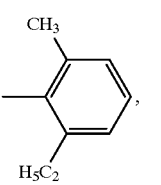

(Z5)
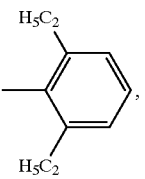

(Z6)
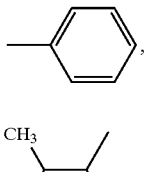

(Z7)
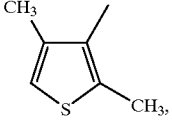

(Z8)
—CH$_2$—C$_3$H$_7$-i, (Z9)
—C$_3$H$_7$-n, (Z10)
—C$_4$H$_9$-n, (Z11)
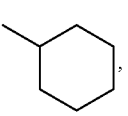

(Z12)
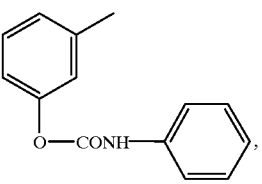

-continued (Z13)

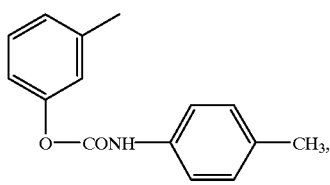

(Z14)

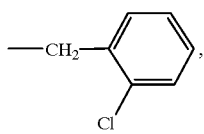

(Z15)

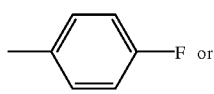

(Z16)

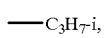

$R_{12}$ is hydrogen, —$CH_2OCH_3$, —$CH_2OC_2H_5$, —CH($CH_3$)$CH_2OCH_3$, —$C_3H_7$-i, —$CH_2$—$C_3H_7$-i, —$C_3H_7$-n, —$CH_3$ or —$C_2H_5$, $R_{13}$ is —$N(CH_3)_2$, —$N(OCH_3)CH_3$, —$CH_2Cl$, —$SC_2H_5$, —$SC_3H_7$-n, —$OCH_3$, —$OC_2H_5$ or

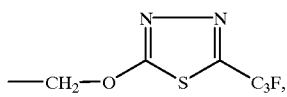

or $R_{13}$ together with $R_{12}$ forms a radical of the formula —O—$CH_2$—$C(CH_3)_2$—CO—,

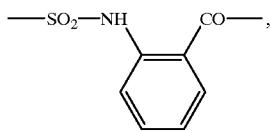

—$CH_2$—$CH(CH_2Cl)$—CHCl—CO— or of the formula VI (VI)

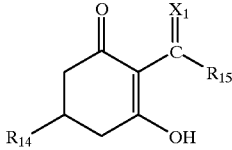

in which
$R_{14}$ is hydrogen or —$CH_2$—$CH(CH_3)$—$SC_2H_5$, $R_{15}$ is —$C_2H_5$, —$C_3H_7$-n or

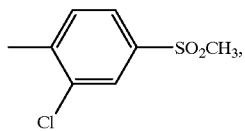

and
$X_1$ is =O, =$NOC_2H_5$ or =$NOCH_2$—CH=CHCl, or of the formula VII (VII)

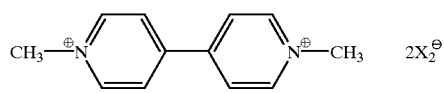

in which
$X_2^{\ominus}$ is $Cl^{\ominus}$ or $CH_3SO_3^{\ominus}$, as a mixture with each other.

It is entirely surprising that the combination of the compound of formula A with at least one compound of formulae I to VII is greater than the expected additive action against the weeds to be controlled and thus in particular enhances the activity range of both components in two respects:

On the one hand, the rates of application of the single compounds are reduced while the effectiveness is retained. On the other hand, the novel herbicidal combination also achieves a high degree of weed control where the single compounds have become no longer agriculturally effective at low rates of application. The consequence is a substantial broadening of the activity spectrum against weeds and an additional increase in the selectivity for the cultivated plants that is necessary and desirable in the event of unintentional overapplication of herbicide.

The novel herbicidal combination can be used against a great number of agriculturally important weeds in crops of cultivated plants, including Veronica, Galium, Papaver, Solanum, Chenopodium, Amaranthus, Xanthium, Abutilon, Ambrosia, Sagitaria, Ipomoea, Cassiastora, *Datura stramonium, Sesbania exaltata* and *Sida spinosa*. Furthermore, it has emerged that, after application of the compositions according to the invention, the compound of the formula A which they comprise is broken down more rapidly in the treated crop plants, in particular maize, than metolachlor, which is an important advantage.

The compositions according to the invention are suitable for all application methods conventionally used in agriculture, for example preemergence application, postemergence application and seed dressing.

The herbicide mixture according to the invention is preferably suitable for controlling weeds in crops of useful plants such as cereals, rape, sugar beet, sugar cane, in plantation crops, in rice, cotton and, in particular, maize and soybeans.

Crops are also to be understood as meaning those which have been made tolerant to herbicides or classes of herbicides by conventional breeding or genetic engineering methods.

The combination of active ingredients according to the invention comprises the active ingredient of the formula A and the active ingredient(s) from the substance classes of the formulae I to VII in any ratio, but as a rule, with an excess of one component over the other. Preferred mixing ratios of the active ingredient of the formula A to the other components are, as a rule, between 120:1 and 1:3.

It has been found that very particularly effective synergistic mixtures of active ingredients are the following combinations:
compound of the formula A+atrazine, compound of the formula A+cyanazine,
compound of the formula A+flumetsulam, compound of the formula A+gluphosinate,
compound of the formula A+glyphosate, compound of the formula A+metosulam,
compound of the formula A+nicosulfuron, compound of the formula A+pendimethalin, compound of the formula A+rimsulfuron, compound of the formula A+sulfosate, compound of the formula A+terbuthylazine or compound of the formula A+2,4-D, compound of the formula A+bromoxynil, compound of the formula A+dicamba, compound of the formula A+halosulfuron, compound of the formula A+metribuzine, compound of the formula A+paraquat, compound of the formula A+primisulfurone, compound of the formula A+prosulfurone, compound of the formula A+pyridate, compound of the formula A+rimsulfuron, compound of the formula A+simazine, compound of the formula A+sulcotrione or compound of the formula A+acetochlor, compound of the formula A+alachlor, compound of the formula A+ametryne, compound of the formula A+bentazone, compound of the formula A+butylate, compound of the formula A+clopyralide, compound of the formula A+BAY FOE 5043, compound of the formula A+dimethenamide, compound of the formula A+EPTC, compound of the formula A+linuron, compound of the formula A+propachlor, compound of the formula A+thifensulfurone, compound of the formula A+trifluralin or compound of the formula A+bensulfurone, compound of the formula A+chlorimuron-ethyl, compound of the formula A+chlorsulfurone, compound of the formula A+metsulfuron-methyl, compound of the formula A+sulfometuron-methyl, compound of the formula A+triasulfurone, compound of the formula A+tribenuron-methyl or compound of the formula A+imazaquin, compound of the formula A+imazethapyr and compound of the formula A+imazapyr.

Preferred amongst these combinations of active ingredients are compound of the formula A+atrazine, compound of the formula A+cyanazine, compound of the formula A+flumetsulam, compound of the formula A+gluphosinate, compound of the formula A+glyphosate, compound of the formula A+metosulam, compound of the formula A+nicosulfuron, compound of the formula A+pendimethalin, compound of the formula A+rimsulfuron, compound of the formula A+sulfosate and compound of the formula A+terbuthylazine.

Another group of preferred combinations of active ingredients embraces compound of the formula A+atrazine, compound of the formula A+terbutylazine, compound of the formula A+flumetsulam, compound of the formula A+pendimethalin, compound of the formula A+metosulam, compound of the formula A+pyridate, compound of the formula A+pyridate+terbutylazine, compound of the formula A+glyphosphate, compound of the formula A+glufosinate, compound of the formula A+oxosulfuron and compound of the formula A+imazethapyr.

A further group of preferred combinations of active ingredients embraces compound of the formula A+cyanazine, compound of the formula A+nicosulfuron, compound of the formula A+rimsulfuron, compound of the formula A+sulfosate, compound of the formula A+dicamba, compound of the formula A+halosulfuron, compound of the formula A+primisulfuron and compound of the formula A+imazaquin.

Also of importance are the combinations compound of the formula A+primisulfuron+dicamba, compound of the formula A+prosulfuron+dicamba, compound of the formula A+prosulfuron+primisulfuron and compound of the formula A+prosulfuron+primisulfuron+dicamba.

The abovementioned combinations of active ingredients are preferably used in crops of maize.

A further group of preferred combinations of active ingredients is the following:

compound of the formula A+2,4-D, compound of the formula A+gluphosinate, compound of the formula A+glyphosate, compound of the formula A+imazaquin, compound of the formula A+imazethapyr, compound of the formula A+metribuzin, compound of the formula A+pendimethalin, compound of the formula A+sulfosate or compound of the formula A+acifluorfen, compound of the formula A+bentazon, compound of the formula A+chlorimuron-ethyl, compound of the formula A+clethodim, compound of the formula A+clodinafop, compound of the formula A+clomazone, compound of the formula A+fenoxaprop, compound of the formula A+fluazifop, compound of the formula A+fomesafen, compound of the formula A+linuron, compound of the formula A+paraquat, compound of the formula A+quizalofop, compound of the formula A+sethoxydim or compound of the formula A+2,4-DB, compound of the formula A+acetochlor, compound of the formula A+alachlor, compound of the formula A+dimethenamide, compound of the formula A+diuron, compound of the formula A+EPTC, compound of the formula A+ethalfluralin, compound of the formula A+imazapyr, compound of the formula A+lactofen, compound of the formula A+norflurazon, compound of the formula A+chloridazon, compound of the formula A+thifensulfuron-methyl, compound of the formula A+trifluralin or compound of the formula A+bensulfuron, compound of the formula A+chlorsulfuron, compound of the formula A+halosulfuron, compound of the formula A+metsulfuron-methyl, compound of the formula A+primisulfuron compound of the formula A+prosulfuron, compound of the formula A+rimsulfuron, compound of the formula A+sulfometuron-methyl, compound of the formula A+triasulfuron, compound of the formula A+BAY FOE 5043, compound of the formula A+cloransulam, compound of the formula A+flumetsulam, compound of the formula A+oxosulfuron and compound of the formula A+tribenuron-methyl.

Amongst these, the preferred combinations of active ingredients are compound of the formula A+2,4-D, compound of the formula A+gluphosinate, compound of the formula A+glyphosate, compound of the formula A+imazaquin, compound of the formula A+imazethapyrm, compound of the formula A+metribuzin, compound of the formula A+pendimethalin and compound of the formula A+sulfosate.

A further group of preferred combinations of active ingredients embraces compound of the formula A+gluphosinate, compound of the formula A+glyphosate, compound of the formula A+imazethapyr, compound of the formula A+pendimethalin, compound of the formula A+oxosulfuron and compound of the formula A+flumetsulam.

The abovementioned combinations of active ingredients are particularly suitable for use in crops of soybeans.

Another group of preferred combinations of active ingredients is compound of the formula A+chloridazon, compound of the formula A+clethodim, compound of the formula A+clodinafop, compound of the formula A+clopyralid, compound of the formula A+cycloate, compound of the formula A+desmedipham, compound of the formula A+endothal, compound of the formula A+EPTC, compound of the formula A+ethofumesate, compound of the formula A+fenoxaprop, compound of the formula A+fluazifop, compound of the formula A+glufosinate, compound of the formula A+glyphosate, compound of the formula A+haloxyfop, compound of the formula A+metamitron, compound of the formula A+pebulate, compound of the formula A+phenmedipham, compound of the formula A+quizalofop, compound of the formula A+sethoxydim, compound of the formula A+sulfosate and compound of the formula A+trifluralin.

These combinations are preferably suitable for use in sugar beet.

Furthermore of importance are the combinations of active ingredients compound of the formula A+clethodim, compound of the formula A+clodinafop, compound of the formula A+cyanazine, compound of the formula A+diuron, compound of the formula A +fenoxaprop, compound of the formula A+fluazifop, compound of the formula A+fluometuron, compound of the formula A+fluorchloridone, compound of the formula A+glufosinate, compound of the formula A+glyphosate, compound of the formula A+haloxyfop, compound of the formula A+norflurazon, compound of the formula A+prometryne, compound of the formula A+pyrithiobac, compound of the formula A+chloridazone, compound of the formula A+quizalofop, compound of the formula A+sethoxydim, compound of the formula A+sulfosate and compound of the formula A+trifluralin, in particular with a view to their application in cotton.

In addition to the compound of the formula A and at least one compound from amongst the substance classes of the formulae I to VII, the synergistic compositions according to the invention can comprise a safener, in particular benoxacor.

The abovementioned active ingredients are described and characterized in "The Pesticide Manual", Tenth Edition, 1994, Crop Protection Publications or in other customary agronomical publications. Oxosulfuron (CGA 277 476) was introduced to the public at the Brighton Crop Protection Conference—Weeds—1995 (Plenary Session 2, Nov. 21, 1995).

The rate of application can vary within a wide range and will depend on the nature of the soil, the type of application (pre- or post-emergence; seed dressing; application to the seed furrow; no-tillage application etc.), the crop plant, the weed to be controlled, the respective prevailing climatic conditions, and on other factors governed by the type and timing of application and the target crop. In general, the mixture of active ingredients according to the invention can be applied in a rate of application of 300 to 4,000 g of mixture of active ingredients/ha.

In the composition according to the invention, the weight ratio of the component of the formula A to at least one compound from amongst the substance classes of the formulae I to VII is from 1:10 to 1:0.001.

If the composition comprises a safener, the weight ratio of herbicide of the formula (A) to safener is preferably 5:1 to 30:1.

The compositions according to the invention can be used in unmodified form, i.e. as obtained by synthesis, but they are preferably processed in a conventional manner with the auxiliaries conventionally employed in the art of formulation, for example to give emulsifiable concentrates, if they are not sulfonylureas, directly sprayable or dilutable solutions, dilute emulsions, wettable powders, soluble powders, dusts, granules or microcapsules. The types of application, such as spraying, atomizing, dusting, wetting, scattering or pouring, and the type of composition are chosen in accordance with the intended objectives and the prevailing circumstances.

The formulations, i.e. the compositions, preparations or products comprising the active ingredients of the formulae A and I, II, III, IV, V, VI or VII and, if desired, a safener and/or one or more solid or liquid formulation auxiliaries, are prepared in a manner known per se, for example by intimately mixing and/or grinding the active ingredients with the formulation auxiliaries, for example solvents or solid carriers. Furthermore, surface-active compounds (surfactants) can additionally be used when preparing the formulations.

Suitable solvents may typically be: aromatic hydrocarbons, preferably the fractions containing 8 to 12 carbon atoms such as mixtures of alkylbenzenes, typically xylene mixtures or alkylated naphthalenes; aliphatic and cycloaliphatic hydrocarbons such as paraffins, cyclohexane or tetrahydronaphthalene; alcohols such as ethanol, propanol or butanol; glycols and their ethers and esters such as propylene glycol or dipropylene glycol ether; ketones such as cyclohexanone, isophorone or diacetone alcohol; strongly polar solvents such as N-methyl-2-pyrrolidone, dimethyl sulfoxide or water, vegetable oils and their esters such as rapeseed oil, castor oil or soybean oil; and in some cases also silicone oils.

The solid carriers typically used for dusts and dispersible powders are usually natural mineral fillers such as calcite, talcum, kaolin, montmorillonite or attapulgite. To improve the physical properties it is also possible to add highly dispersed silicic acid or highly dispersed absorbent polymers. Suitable granulated adsorptive carriers are porous types, including pumice, broken brick, sepiolite or bentonite; and suitable nonsorbent carriers are materials such as calcite or sand. In addition, innumerable pregranulated materials of inorganic or organic origin may be used, especially dolomite or pulverised plant residues.

Depending on the type of compound of formula I to be formulated, suitable surface-active compounds are nonionic, cationic and/or anionic surfactants having good emulsifying, dispersing and wetting properties. Surfactants will also be understood as comprising mixtures of surfactants.

Suitable anionic surfactants may be water-soluble soaps as well as water-soluble synthetic surface-active compounds.

Suitable soaps are the alkali metal salts, alkaline earth metal salts, ammonium salts or substituted ammonium salts of higher fatty acids ($C_{10}$–$C_{22}$), e.g. the sodium or potassium salts of oleic or stearic acid, or of natural fatty acid mixtures which can be obtained, inter alia from coconut oil or tallow oil. Further suitable soaps are also the fatty acid methyl taurin salts.

More often, however, so-called synthetic surfactants are used, especially fatty sulfonates, fatty sulfates, sulfonated benzimidazole derivatives or alkylarylsulfonates.

The fatty alcohol sulfonates or sulfates are usually in the form of alkali metal salts, alkaline earth metal salts, ammonium salts or substituted ammonium salts, and they contain a $C_8$–$C_{22}$alkyl radical which also includes the alkyl moiety of acyl radicals, e.g. the sodium or calcium salt of ligninsulfonic acid, of dodecylsulfate, or of a mixture of fatty alcohol sulfates obtained from natural fatty acids. These compounds also comprise the salts of sulfated or sulfonated fatty alcohol/ethylene oxide adducts. The sulfonated benzimidazole derivatives preferably contain 2 sulfonic acid groups and one fatty acid radical containing 8 to 22 carbon atoms. Illustrative examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Corresponding phosphates, typically salts of the phosphoric acid ester of an adduct of p-nonylphenol with 4 to 14 mol of ethylene oxide, or phospholipids, are also suitable.

Nonionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable nonionic surfactants are the water-soluble polyadducts of polyethylene oxide with polypropylene glycol, ethylenediaminopolypropylene glycol and alkylpolypropylene glycol containing 1 to 10 carbon atoms in the alkyl chain, which polyadducts contain 20 to 250 ethylene glycol ether groups and 10 to 100 propylene glycol ether groups. These compounds usually contain 1 to 5 ethylene glycol units per propylene glycol unit.

Illustrative examples of nonionic surfactants are nonylphenol polyethoxylates, polyethoxylated castor oil, polyadducts of polypropylene and polyethylene oxide, tributylphenol polyethoxylate, polyethylene glycol and octylphenol polyethoxylate.

Fatty acid esters of polyoxyethylene sorbitan are also suitable nonionic surfactants, typically polyoxyethylene sorbitan trioleate.

Cationic surfactants are preferably quaternary ammonium salts carrying, as N-substituent, at least one $C_8$–$C_2$alkyl radical and, as further substituents, optionally halogenated lower alkyl, benzyl or hydroxy-lower alkyl radicals. The salts are preferably in the form of halides, methyl sulfates or ethyl sulfates, for example stearyl trimethylammonium chloride or benzyl bis(2-chloroethyl)ethylammonium bromide.

The surfactants customarily employed in the art of formulation are described, inter alia, in "Mc Cutcheon's Detergents and Emulsifiers Annual", Mc Publishing Corp., Glen Rock, N.J. 1988, H. Stache, "Tensid-Taschenbuch" (Handbook of Surfactants), Carl Hanser Verlag, Munich/Vienna 1981, and M. and J. Ash, "Encyclopedia of Surfactants", Vol I–III, Chemical Publishing Co., N.Y., 1980–81.

The herbicidal compositions will usually contain from 0.1 to 99% by weight, preferably from 0.1 to 95% by weight, of a combination of the compound of formula A with the compounds of formula I, II, III, IV, V, VI or VII, from 1 to 99.9% by weight of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

The formulations may also contain further ingredients such as stabilisers, vegetable oils or epoxidised vegetable oils, (epoxidised coconut oil, rapeseed oil or soybean oil), antifoams, typically silicone oil, preservatives, viscosity regulators, binders, tackifiers, as well as fertilisers or other chemical agents.

In particular, preferred formulations are made up as follows (throughout, percentages are by weight):

Emulsifiable Concentrates
  herbicidal combination: 1 to 90%, preferably 5 to 20%
  surfactant: 1 to 30%, preferably 10 to 20%
  liquid carrier: 5 to 94%, preferably 70 to 85%
Dusts
  herbicidal combination: 0.1 to 10%, preferably 0.1 to 5%
  solid carrier: 99.9 to 90%, preferably 99.9 to 99%
Suspension Concentrates
  herbicidal combination: 5 to 75%, preferably 10 to 50%
  water: 94 to 24%, preferably 88 to 30%
  surfactant: 1 to 40%, preferably 2 to 30%
Wettable Powders
  herbicidal combination: 0.5 to 90%, preferably 1 to 80%
  surfactant: 0.5 to 20%, preferably 1 to 15%
  solid carrier: 5 to 95%, preferably 15 to 90%
Granulates
  herbicidal combination: 0.1 to 30%, preferably 0.1 to 15%
  solid carrier: 99.5 to 70%, preferably 97 to 85%

The invention is illustrated by the following non-limitative Examples.

FORMULATION EXAMPLES

Combinations of the Compounds of Formulae A, I, II, III, IV, V, VI or VII (Throughout, Percentages are by Weight)

| F1. Emulsifiable concentrates | a) | b) | c) | d) |
|---|---|---|---|---|
| combination of a compound of formula A and a herbicide of formulae I to VII | 5% | 10% | 25% | 50% |
| calcium dodecylbenzenesulfonate | 6% | 8% | 6% | 8% |
| polyethoxylated castor oil (36 mol EO) | 4% | — | 4% | 4% |
| octylphenol polyethoxylate (7–8 mol EO) | — | 4% | — | 2% |
| cyclohexanone | — | — | 10% | 20% |
| mixture of aromatic hydrocarbons $C_9$—$C_{12}$ | 85% | 78% | 55% | 16% |

Emulsions of any desired concentration can be prepared by diluting such concentrates with water.

| F2. Solutions | a) | b) | c) | d) |
|---|---|---|---|---|
| combination of a compound of formula A and a herbicide of formula I to VII | 5% | 10% | 50% | 90% |
| 1-methoxy-3-(3-methoxypropoxy)-propane | — | 20% | 20% | — |
| polyethylene glycol 400 | 20% | 10% | — | — |
| N-methyl-2-pyrrolidone | — | — | 30% | 10% |
| mixture of aromatic hydrocarbons $C_9$—$C_{12}$ | 75% | 60% | — | — |

The solutions are suitable for use as microdrops.

| F3. Wettable powders | a) | b) | c) | d) |
|---|---|---|---|---|
| combination of a compound of formula A and a herbicide of formula I to VII | 5% | 25% | 50% | 80% |

| F3. Wettable powders | a) | b) | c) | d) |
|---|---|---|---|---|
| sodium ligninsulfonate | 4% | — | 3% | — |
| sodium laurylsulfate | 2% | 3% | — | 4% |
| sodium diisobutylnaphthalene sulfonate | — | 6% | 5% | 6% |
| octylphenol polyethoxylate (7–8 mol EO) | — | 1% | 2% | — |
| highly dispersed silica | 1% | 3% | 5% | 10% |
| kaolin | 88% | 62% | 35% | — |

The compound mixture is thoroughly mixed with the adjuvants and this mixture is ground in a suitable mill to give wettable powders which can be diluted with water to give suspensions of any desired concentration.

| F4. Coated granulates | a) | b) | c) |
|---|---|---|---|
| combination of a compound of formula A and a herbicide of formula I to VII | 0.1% | 5% | 15% |
| highly dispersed silica | 0.9% | 2% | 2% |
| inorganic carrier (Ø 0.1–1 mm) e.g. CaCO$_3$ or SiO$_2$ | 99.0% | 93% | 83% |

The compound mixture is dissolved in methylene chloride, the solution is sprayed on to the carrier, and the solvent is removed under vacuum.

| F5. Coated granulates | a) | b) | c) |
|---|---|---|---|
| combination of a compound of formula A and a herbicide of formula I to VII | 0.1% | 5% | 15% |
| polyethylene glycol 200 | 1.0% | 2% | 3% |
| highly dispersed silica | 0.9% | 1% | 2% |
| inorganic carrier (Ø 0.1–1 mm) e.g. CaCO$_3$ or SiO$_2$ | 98.0% | 92% | 80% |

The finely ground compound mixture is uniformly applied in a mixer to the kaolin moistened with polyethylene glycol. Non-dusty coated granulates are obtained in this manner.

| F6. Extruder granulates | a) | b) | c) | d) |
|---|---|---|---|---|
| combination of a compound of formula A and a herbicide of formula I to VII | 0.1% | 3% | 5% | 15% |
| sodium ligninsulfonate | 1.5% | 2% | 3% | 4% |
| carboxymethyl cellulose | 1.4% | 2% | 2% | 2% |
| kaolin | 97.0% | 93% | 90% | 79% |

The compound mixture is mixed with the adjuvants and the mixture is moistened with water. This mixture is extruded and then dried in a stream of air.

| F7. Dusts | a) | b) | c) |
|---|---|---|---|
| combination of a compound of formula A and a herbicide of formula I to VII | 0.1% | 1% | 5% |
| talcum | 39.9% | 49% | 35% |
| kaolin | 60.0% | 50% | 60% |

Ready for use dusts are obtained by mixing the compound mixture with the carriers on a suitable mill.

| F8. Suspension concentrates | a) | b) | c) | d) |
|---|---|---|---|---|
| combination of a compound of formula A and a herbicide of formula I to VII | 3% | 10% | 25% | 50% |
| ethylene glycol | 5% | 5% | 5% | 5% |
| nonylphenol polyethoxylate (15 mol EO) | — | 1% | 2% | — |
| sodium ligninsulfonate | 3% | 3% | 4% | 5% |
| carboxymethyl cellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground compound mixture is homogeneously mixed with the adjuvants to give a suspension concentrate from which suspensions of any desired concentration can be prepared by dilution with water.

It is often more expedient to formulate the compound of formula A and the components of formula I to VII individually and only to combine them shortly before application in the applicator in the desired mixture ratio as tank mixture.

It can further prove advantageous to apply the active ingredient of the formula A, if desired in combination with the safener; separated in time from one or more active ingredients of the formulae I to VII. It is also possible to apply the active ingredient of the formula A separated in time from one or more active ingredients of the formulae I to VII, if desired in combination with the safener. The results obtained for the compositions according to the invention show an increased selectivity with respect to the crop plants in comparison to corresponding mixtures as in the above-mentioned Research Disclosure.

BIOLOGICAL EXAMPLES

Example B1

Postemergence Test

Monocotyledon and dicotyledon test plants are grown in the greenhouse in plastic pots containing standard soil and, at the 4- to 6-leaf stage, sprayed with an aqueous suspension of the test substances prepared from a 25% wettable powder (Example F3.), which corresponds to a dose of 2,000 g of a.i./ha (500 l of water/ha). The test plants are then grown on in the greenhouse under optimal conditions. After a test period of approximately 18 days, the test is evaluated using a nine-step assessment scale (1 =complete damage, 9=no action). Assessment grades from 1 to 4 (in particular 1 to 3) describe a good to very good herbicidal action. In this test, the compositions according to the invention have a potent herbicidal action. The same results are obtained when the compositions according to the invention are formulated as described in Examples F1 to F2 and F4 to F8.

Example B2

Herbicidal Action Before Emergence of the Plants

Monocotyledon and dicotyledon test plants are sown in plastic pots in standard soil. Immediately after sowing, the test substances are sprayed on in the form of an emulsion concentrate (Example F1.) in the dose shown in Table 1 (500 l of water/ha). The test plants are subsequently grown in the greenhouse under optimal conditions. After a test period of 4 weeks, the test is evaluated: 100% means complete damage, 0% means no action. 100% to 80% and, in particular, 100 to 85%, describe a good to very good herbicidal action.

TABLE 1

| Compound of the formula A in g/ha<br>Other component in g/ha | | | | | |
|---|---|---|---|---|---|
| A in g/ha | 600 | 400 | 200 | 100 | 50 |
| Flumetsulam in g/ha | 30 | 30 | 30 | 30 | 30 |
| Maize | 10 | 0 | 0 | 0 | 0 |
| Cyperus | 80 | 60 | 60 | 30 | 20 |
| Panicum | 95 | 95 | 70 | 30 | 0 |
| Metolachlor in g/ha<br>Other component in g/ha | | | | | |
| Metolachlor in g/ha | 600 | 400 | 200 | 100 | 50 |
| Flumetsulam in g/ha | 30 | 30 | 30 | 30 | 30 |
| Maize | 10 | 0 | 0 | 0 | 0 |
| Cyperus | 70 | 50 | 20 | 20 | 20 |
| Panicum | 98 | 70 | 60 | 30 | 30 |

TABLE 2

| Compound of the formula A in g/ha<br>Other component in g/ha | | | | | |
|---|---|---|---|---|---|
| A in g/ha | 600 | 400 | 200 | 100 | 50 |
| Imazethapyr in g/ha | 30 | 30 | 30 | 30 | 30 |
| Maize | 20 | 20 | 20 | 20 | 20 |
| Brachiaria | 100 | 100 | 95 | 95 | 95 |
| Cyperus | 100 | 100 | 70 | 60 | 60 |
| Panicum | 100 | 100 | 95 | 90 | 90 |
| Metolachlor in g/ha<br>Other component in g/ha | | | | | |
| Metolachlor in g/ha | 600 | 400 | 200 | 100 | 50 |
| Imazethapyr in g/ha | 30 | 30 | 30 | 30 | 30 |
| Maize | 25 | 25 | 20 | 20 | 20 |
| Brachiaria | 100 | 95 | 95 | 85 | 75 |
| Cyperus | 100 | 70 | 70 | 60 | 60 |
| Panicum | 98 | 95 | 80 | 80 | 80 |

TABLE 3

| Compound of the formula A in g/ha<br>Other component in g/ha | | | | | |
|---|---|---|---|---|---|
| A in g/ha | 600 | 400 | 200 | 100 | 50 |
| Oxosulfuron in g/ha | 30 | 30 | 30 | 30 | 30 |
| Maize | 80 | 70 | 70 | 70 | 70 |
| Brachiaria | 98 | 98 | 95 | 90 | 90 |
| Cyperus | 100 | 80 | 60 | 50 | 20 |
| Panicum | 98 | 98 | 95 | 60 | 50 |
| Metolachlor in g/ha<br>Other component in g/ha | | | | | |
| Metolachlor in g/ha | 600 | 400 | 200 | 100 | 50 |
| Oxosulfuron in g/ha | 30 | 30 | 30 | 30 | 30 |
| Maize | 80 | 70 | 75 | 75 | 70 |
| Brachiaria | 90 | 98 | 80 | 80 | 80 |
| Cyperus | 95 | 40 | 30 | 20 | 20 |
| Panicum | 98 | 90 | 90 | 60 | 60 |

TABLE 4

| Compound of the formula A in g/ha<br>Other component in g/ha | | | | | |
|---|---|---|---|---|---|
| A in g/ha | 600 | 400 | 200 | 100 | 50 |
| Pendimethalin in g/ha | 125 | 125 | 125 | 125 | 125 |
| Maize | 0 | 0 | 0 | 0 | 0 |
| Cyperus | 70 | 70 | 50 | 30 | 0 |
| Panicum | 100 | 95 | 95 | 95 | 95 |
| Metolachlor in g/ha<br>Other component in g/ha | | | | | |
| Metolachlor in g/ha | 600 | 400 | 200 | 100 | 50 |
| Pendimethalin in g/ha | 125 | 125 | 125 | 125 | 125 |
| Maize | 0 | 0 | 0 | 0 | 0 |
| Cyperus | 60 | 50 | 40 | 20 | 0 |
| Panicum | 100 | 95 | 95 | 80 | 80 |

The compositions according to the invention have a pronounced herbicidal action. The same results are obtained when the compositions according to the invention are formulated as described in Examples F2 to F8.

Example B3
Combination of Pre- and Postemergence Herbicidal Action

Monocotyledon and dicotyledon test plants are sown in standard soil in plastic pots.

Immediately after sowing, each of them is sprayed with the compound of the formula A as an emulsion concentrate (Example F1.) in the dose shown in Table 2 (500 l of water/ha). The test plants are then grown in the greenhouse under optimal conditions. When the plants have reached the 2- to 3-leaf stage (fully developed leaves of the reference plant maize), they are sprayed with component 2 of the test combination, prepared from one of the abovementioned formulations F2 to F8, in the dose mentioned in the table (500 l of water/ha). The test plants are then grown on under optimal conditions. After a test period of approximately 5 weeks, the test is evaluated: 100% describes complete damage, 0% no action. 100% to 80% and, in particular, 100 to 85%, describe a good to very good herbicidal action. Tables 5 to 9: Combination of pre- and postemergence application

TABLE 5

| Compound of the formula A in g/ha<br>Other component in g/ha | | | | |
|---|---|---|---|---|
| A in g/ha | 600 | 400 | 200 | 100 |
| Atrazine in g/ha | 600 | 400 | 200 | 100 |
| Maize | 0 | 0 | 0 | 0 |
| Brachiaria | 80 | 95 | 45 | 20 |
| Sorghum bic. | 95 | 95 | 45 | 20 |
| Metolachlor in g/ha<br>Other component in g/ha | | | | |
| Metolachlor in g/ha | 600 | 400 | 200 | 100 |
| Atrazine in g/ha | 600 | 400 | 200 | 100 |
| Maize | 10 | 0 | 0 | 0 |
| Brachiaria | 70 | 55 | 5 | 0 |
| Sorghum bic. | 75 | 45 | 5 | 0 |

TABLE 6

| Compound of the formula A in g/ha<br>Other component in g/ha | | | | |
|---|---|---|---|---|
| A in g/ha | 600 | 400 | 200 | 100 |
| Metosulam in g/ha | 120 | 60 | 30 | 15 |
| Maize | 5 | 5 | 0 | 0 |
| Brachiaria | 97 | 60 | 30 | 30 |
| Sorghum bic. | 85 | 80 | 30 | 30 |
| Metolachlor in g/ha<br>Other component in g/ha | | | | |
| Metolachlor in g/ha | 600 | 400 | 200 | 100 |
| Metosulam in g/ha | 120 | 60 | 30 | 15 |
| Maize | 0 | 0 | 0 | 0 |

TABLE 6-continued

| | | | | |
|---|---|---|---|---|
| Brachiaria | 90 | 35 | 5 | 0 |
| Sorghum bic. | 85 | 40 | 5 | 0 |

TABLE 7

| Compound of the formula A in g/ha Other component in g/ha | | | | |
|---|---|---|---|---|
| A in g/ha | 600 | 400 | 200 | 100 |
| Terbuthylazine in g/ha | 600 | 400 | 200 | 100 |
| Maize | 0 | 0 | 0 | 0 |
| Brachiaria | 60 | 50 | 15 | 0 |
| Sorghum bic. | 60 | 50 | 15 | 0 |
| Metolachlor in g/ha Other component in g/ha | | | | |
| Metolachlor in g/ha | 600 | 400 | 200 | 100 |
| Terbuthylazine in g/ha | 600 | 400 | 200 | 100 |
| Maize | 0 | 0 | 0 | 0 |
| Brachiaria | 55 | 20 | 5 | 0 |
| Sorghum bic. | 35 | 20 | 5 | 0 |

TABLE 8

| Compound of the formula A in g/ha Other component in g/ha | | | | |
|---|---|---|---|---|
| A in g/ha | 600 | 400 | 200 | 100 |
| Glyphosate in g/ha | 600 | 400 | 200 | 100 |
| Maize | 15 | 10 | 0 | 0 |
| Brachiaria | 100 | 95 | 40 | 15 |
| Sorghum bic. | 100 | 98 | 80 | 20 |
| Metolachlor in g/ha Other component in g/ha | | | | |
| Metolachlor in g/ha | 600 | 400 | 200 | 100 |
| Glyphosate in g/ha | 600 | 400 | 200 | 100 |
| Maize | — | 20 | 5 | 0 |
| Brachiaria | — | 95 | 40 | 0 |
| Sorghum bic. | — | 98 | 30 | 0 |

TABLE 9

| Compound of the formula A in g/ha Other component in g/ha | | | | |
|---|---|---|---|---|
| A in g/ha | 70 | 35 | 17 | 8.5 |
| Imazethapyr in g/ha | 500 | 250 | 125 | 60 |
| Maize | 10 | 0 | 0 | 0 |
| Brachiaria | 100 | 95 | 60 | 40 |
| Sorghum bic. | 100 | 90 | 80 | 60 |
| Metolachlor in g/ha Other component in g/ha | | | | |
| Metolachlor in g/ha | 70 | 35 | 17 | 8.5 |
| Imazethapyr in g/ha | 500 | 250 | 125 | 60 |
| Maize | 10 | 0 | 0 | 0 |
| Brachiaria | 98 | 60 | 40 | 10 |
| Sorghum bic. | 95 | 90 | 60 | 50 |

The compositions according to the invention have a pronounced herbicidal action. The same results are obtained when the compositions according to the invention are formulated as shown in Examples F2 to F8.

What is claimed is:

1. A herbicidal composition comprising a compound of the formula

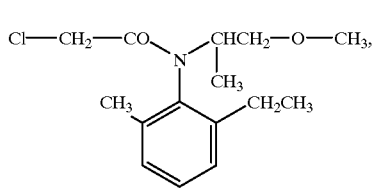

(A)

and at least one additional herbicidally active ingredient selected from the group consisting of atrazine, terbuthylazine, flumetsulam, pendimethalin, metosulam, pyridate, glyphosate, gluphosinate, cyanazine, dicamba, halosulfuron, prosulfuron, primisulfuron, sulcotrione, metribuzin, BAY FOE 5043; and salts thereof.

2. A herbicidal composition according to claim 1, which further comprises an antidotally effective amount of benoxacor.

3. A herbicidal composition according to claim 1, wherein the compound of formula A and the at least one additional active ingredient are present in a weight ratio of from 1:10 to 1:0.001.

4. A herbicidal composition according to claim 1, which comprises a compound of the formula A, atrazine and flumetsulam.

5. A herbicidal composition according to claim 4, which further comprises an antidotally effective amount of benoxacor.

6. A herbicidal composition according to claim 1, which comprises a compound of the formula A, atrazine and dicamba.

7. A herbicidal composition according to claim 6, which further comprises an antidotally effective amount of benoxacor.

8. A herbicidal composition according to claim 1, which comprises a compound of the formula A, prosulfuron and primisulfuron.

9. A method of controlling undesirable plant growth in crops of useful plants, which comprises exposing the crop plant or its environment to a herbicidally active amount of a composition according to claim 1.

10. A method according to claim 9, wherein the crop plants are cereals, rice, oilseed rape, sugar beet, sugar cane, plantation crops, cotton and, in particular, maize and soybeans.

11. A method according to claim 9, wherein the crops of useful plants are treated with the abovementioned composition at rates of application which correspond to 0.3 to 4.0 kg of the total amount of active ingredient per hectare.

12. A method according to claim 9, wherein the exposure of the crop plant or its environment to the compound of the formula A is separated in time from exposure to at least one additional herbicidally active ingredient selected from the group consisting of atrazine, terbuthylazine, flumetsulam, pendimethalin, metosulam, pyridate, glyphosate, gluphosinate, cyanazine, dicamba, halosulfuron, prosulfuron, primisulfuron, sulcotrione, metribuzin, BAY FOE 5043; and salts thereof.

13. A method according to claim 9, which further comprises exposing the crop plant or its environment to an antidotally effective amount of benoxacor.

* * * * *